(12) United States Patent
McLane et al.

(10) Patent No.: US 9,097,584 B2
(45) Date of Patent: *Aug. 4, 2015

(54) METHOD AND APPARATUS FOR DETECTING CADMIUM WITH OPTICAL EMISSION SPECTROSCOPY

(71) Applicant: LINCOLN GLOBAL, INC., City of Industry, CA (US)

(72) Inventors: John Edward McLane, Southhaven, MS (US); Corwin Miller, Brecksville, OH (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,393

(22) Filed: Apr. 8, 2014

(65) Prior Publication Data

US 2014/0218728 A1 Aug. 7, 2014

Related U.S. Application Data

(63) Continuation of application No. 12/835,987, filed on Jul. 14, 2010, now Pat. No. 8,730,470.

(51) Int. Cl.
*G01J 3/28* (2006.01)
*G01J 3/443* (2006.01)
*G01N 21/31* (2006.01)
*G01N 21/67* (2006.01)

(52) U.S. Cl.
CPC ............... *G01J 3/443* (2013.01); *G01N 21/31* (2013.01); *G01N 21/67* (2013.01); *G01J 2003/2879* (2013.01)

(58) Field of Classification Search
USPC ......................................... 356/326
See application file for complete search history.

(56) References Cited

U.S. PATENT DOCUMENTS

| | | | |
|---|---|---|---|
| 5,391,270 A * | 2/1995 | Gui et al. | 205/789.5 |
| 2001/0042693 A1 * | 11/2001 | Onitskansky et al. | 205/780 |
| 2006/0160205 A1 * | 7/2006 | Blackburn et al. | 435/287.2 |
| 2006/0235646 A1 | 10/2006 | Fathallah-Shaykh | |
| 2008/0173810 A1 | 7/2008 | Morrisroe | |
| 2009/0071232 A1 | 3/2009 | Hartle et al. | |
| 2010/0267942 A1 | 10/2010 | Buchanan et al. | |

* cited by examiner

*Primary Examiner* — Abdullahi Nur
(74) *Attorney, Agent, or Firm* — Perkins Coie LLP

(57) ABSTRACT

An apparatus and method for detecting cadmium using optical emission spectroscopy is provided. The apparatus contains a system which uses optical emission spectroscopy which is programmed and calibrated to detect the presence of cadmium in PPM. The system is calibrated using test samples which have been prepared with a lead/cadmium matrix material having at least one iron based electrode integrated therein.

18 Claims, 3 Drawing Sheets

METHOD AND APPARATUS FOR DETECTING CADMIUM WITH OPTICAL EMISSION SPECTROSCOPY

PRIORITY DATA AND INCORPORATION BY REFERENCE

This application is a continuation of prior U.S. application Ser. No. 12/835,987, filed Jul. 14, 2010, which is incorporated herein by reference in its entire.

BACKGROUND OF THE INVENTION

1. Field of the Invention

Devices, systems, and methods consistent with the invention relate to a method and apparatus for detecting cadmium with optical emission spectroscopy.

2. Description of the Related Art

As is widely known in the welding industry, the presence of cadmium in weld metal and welding electrodes is undesirable and many efforts have been implemented to greatly reduce or eliminate cadmium from weld metal. In this regard various entities which govern welding standards have instituted standards which require those who manufacture welding electrodes to certify the amount of cadmium present in their welding electrodes. For example, in Europe, an electrode manufacturer must certify that the use of their electrodes will not result in a weld metal having more than 100 parts per million (PPM) of cadmium.

This certification requires an electrode manufacturer to conduct significant amounts of testing to provide the appropriate certification. To date this testing has been done using inductively-coupled plasma testing with mass spectroscopy (ICP-MS) to test weld metal for the presence of cadmium. This process entails liquefying a test sample in an acid solution, and then testing the liquefied sample for the presence of various elements, including cadmium. Not only is this process highly toxic, but it is also very inefficient as it takes a few hours to conduct a test on a single sample. Because of the frequent need to certify welding electrodes, a need exists to accelerate the certification process.

BRIEF SUMMARY OF THE INVENTION

An exemplary embodiment of the present invention is a method of detecting cadmium in a sample using an optical emission spectrometer. The method includes preparing at least one calibration sample which contains a first element, at least one of lead, thallium and zinc, and a preselected amount of cadmium and calibrating the optical emission spectrometer to detect an amount of cadmium using the calibration sample. The method also includes using the calibrated optical emission spectrometer to detect an amount of cadmium within a sample, such as a weld sample.

BRIEF DESCRIPTION OF THE DRAWINGS

The above and/or other aspects of the invention will be more apparent by describing in detail exemplary embodiments of the invention with reference to the accompanying drawings, in which.

DETAILED DESCRIPTION OF EXEMPLARY EMBODIMENTS

Figure 1A:
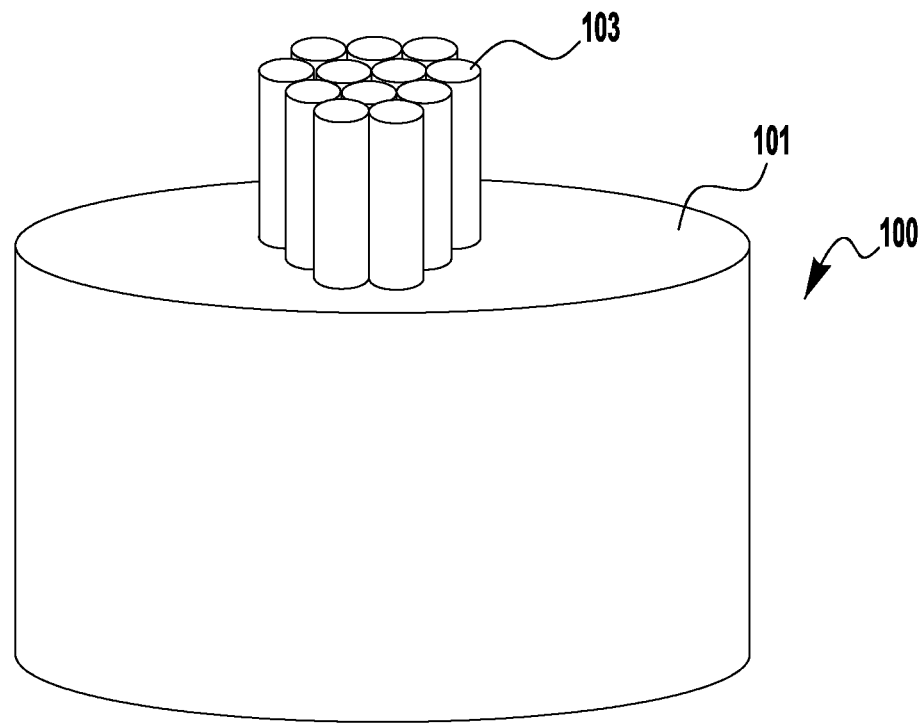
FIGS. 1A and 1B illustrate diagrammatical representations of an exemplary embodiment of test sample employed in accordance with an embodiment of the present invention.

Exemplary embodiments of the invention will now be described below by reference to the attached Figures. The described exemplary embodiments are intended to assist the understanding of the invention, and are not intended to limit the scope of the invention in any way. Like reference numerals refer to like elements throughout.

Exemplary embodiments of the present invention employ optical emission spectroscopy (OES) and the various devices and machines which are capable of performing this type of material analysis. Optical emission spectrometers (OES) are known and their use to detect the elemental composition of samples is known. OES machines generate plasma at the surface of a test sample (which must be electrically conductive) to create a very high light intensity. This light is then reflected from the surface of the sample in various wavelengths, where the wavelengths are related to and represent the various elements present in the sample. See Table 1 (below) showing various wavelengths for different elements. These wavelengths are known to those of skill in the art. The benefit of employing OES technology as opposed to ICP technology is that OES technology can complete the test in a few minutes as opposed to a few hours. Additionally, the testing is considerably less toxic.

However, the use of OES machines in the welding industry is limited because of the inherent limitations to date in being able to properly calibrate or configure OES-type systems to detect cadmium in PPM in a sample.

As stated, OES machines are known and can be used to detect many elements/chemicals present in a test sample. However, to date OES machines have been unable to detect the PPM of cadmium in a metallic sample. This is primarily because the manufacturers of OES machines have been unable to program or otherwise calibrate the OES machines to detect the PPM of cadmium in a sample.

This inability to calibrate OES machines stems from the specific material properties of cadmium, relative to other materials such as steel or iron.

To obtain the necessary certifications, OES machines use iron as a base line, to which the presence of all other elements in a sample are compared. In at least some OES machines the test sample must contain at least 40% iron by mass of the sample.

Accordingly, to sufficiently calibrate an OES machine to detect cadmium it is necessary to create test samples having at least iron and cadmium. To date this has not been done.

The typical method of making test samples, for use in OES machines, and the like, is to create a molten pool into which all of the materials are placed, and when the pool solidifies a uniform sample is created and tested. This typical methodology can not be employed when using iron and cadmium because cadmium's melting temperature (about 321 degrees C.) is considerable less than that of iron (about 1535 degrees C.). Therefore, if the prior methodology of making a sample is employed the cadmium is vaporized before the iron is sufficiently melted to create a test sample. Because of this, it has not been possible to create samples to calibrate an OES machine to detect cadmium in a metallic sample. Because proper samples could not be created, OES machines could not be calibrated to detect the PPM of cadmium in a sample and thus could not have been used for cadmium certifications in the welding industry.

Figure 1B:
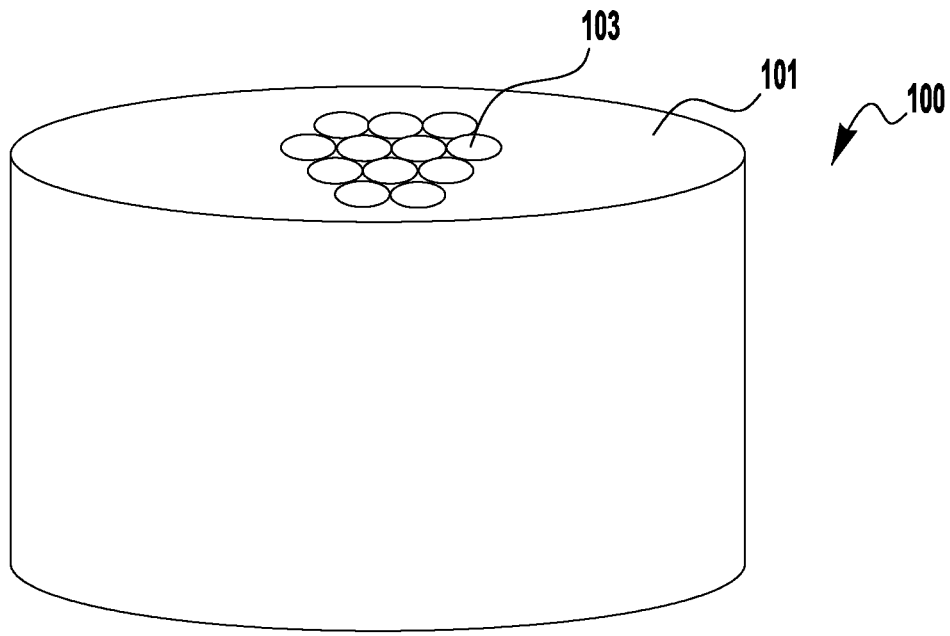

Turning now to FIGS. 1A and 1B, a test sample in accordance with an exemplary embodiment of the present invention has been shown. Specifically, these figures depict a test sample 100 at two different stages. As shown in FIG. 1A the test sample 100 comprises a matrix portion 101 and a plurality of iron or steel based electrodes 103. The matrix portion 101 is made up of a combination of lead and cadmium and the electrodes 103 can be any commonly known or used steel or iron based welding electrode, which is copper coated.

The matrix portion 101 is made up of lead and cadmium because lead has a melting temperature (about 328 degrees C.) which is similar to that of cadmium. Accordingly, there is no issue of cadmium vaporization when the matrix portion 101 is made. The electrodes 103 are steel or iron based so as to provide the iron base line needed when employing OES machines, as described above. The number and type of electrodes 103 are such that the needed percentage of iron is present in the test sample 100 when its manufacture is completed. For example, in an embodiment of the present invention the test sample must contain at least 40% iron by mass. Therefore, the number and type of electrodes 103 employed must satisfy that criteria when the sample 100 is completed.

It is noted that although the electrodes 103 have been identified as welding electrodes, the present invention is not limited in this regard. Any acceptable substitute can be employed which will provide the needed amount of iron and which will sufficiently bond with the lead/cadmium matrix 101. For example, a single large iron specimen can be utilized. Further, the shape of the electrode or specimen 103 is not limiting.

An exemplary method of manufacturing the sample 100 will now be described. A size of the sample 100 is to be selected and a mold prepared accordingly. In an embodiment of the present invention, the sample has a circular cross-section with a diameter of at least 6 mm. However, for purposes of the present invention, the size and shape of the sample 100 is not intended to be limiting. Then a molten mixture of lead and a preselected amount of cadmium is placed into the mold. Because lead and cadmium melt at approximately the same temperature, creating the molten matrix material is within the knowledge of those skilled in the art. The amount of cadmium should be preselected so as to obtain a desired amount by mass of cadmium for the sample 100. For example, if it is desired that the sample is to have 1% by mass of cadmium, the appropriate amount of cadmium relative to the lead and other components should be added to the molten mixture of the matrix 101.

Once the material of the matrix 101 is completely molten and in such a state that the cadmium is evenly distributed throughout the matrix 101, the electrodes/specimen 103 can be placed into the molten matrix 101. This is done by inserting the electrodes/specimen 103 fully into the matrix 101. Then the matrix 101 is allowed to cool around the electrodes 103 so as to create a solidified test sample 100. Additionally, the molten matrix can be poured over and around the bundle of material.

In the embodiment shown, in which a plurality of electrodes are employed, the electrodes 103 are to be configured in a tight bundle, as shown, and the matrix material should penetrate all gaps, if any, between the electrodes 103. Additionally, because it is difficult to bond lead to steel or iron, in an embodiment of the invention, the electrodes 103 (or whatever iron delivery system is used) are coated with copper. This is because it is easier for the lead/cadmium matrix to bond to a copper surface than a steel/iron surface. Of course, any other metal may be used to coat the electrodes/specimen 103 so long as it displays sufficient bonding characteristics to both lead/cadmium and iron/steel. Further, the material should display sufficient electrically conductivity.

During cooling of the matrix portion 101, pressure should be continuously applied to the electrodes/specimen 103 to ensure that they do not tend to float out of the matrix. This can occur due to the density differential between the lead/cadmium matrix and the steel/iron electrodes.

As indicated above, the electrodes 103 can be replaced with any iron delivery system which is capable of sufficiently delivering the proper amount of iron needed for a reliable test. For example, an iron or steel ingot can be used; iron or steel rods or specimens can be used; etc. Steel can be used because of the presence of iron in the steel. Of course, a sufficient amount of steel should be employed so that the requisite amount, by mass, of iron is obtained.

Further, as indicated above, in an embodiment of the invention the electrodes 103 (or alternative iron delivery system) are copper coated electrodes to enable sufficient bonding. Alternative coatings can be employed so long as they provide suitable bonding between the lead/cadmium matrix 101 and the electrodes 103 (are whatever is used).

It is noted that in another embodiment of the present invention, zinc or thallium can be used as an alternative to lead, or can be used in conjunction with lead as described herein. However, because thallium is a toxic substance, great care should be taken if thallium is employed.

Once the matrix 101 has sufficiently cooled and hardened, the sample 100 can be prepared in any appropriate manner for purposes of the OES testing. For example, the portions of the electrodes 103 (or alternative iron delivery system) which protrude above the surface of the matrix can be removed and then the surface of the sample 100 polished and buffed as needed. Further, the sample 100 should be inspected to ensure that no gaps exist between the electrodes/specimen 103 or otherwise within the matrix 101.

Once the sample 100 is appropriately prepared, it is placed within the appropriate portion of the OES machine. As is known, an OES machine uses plasma "sparks" to generate a high intensity light which is directed towards the test surface of the sample 100. This light is reflected from the surface in varying wavelengths which represent the elements present in the sample. The OES machine then registers and records the signal intensity of the light in each wavelength reflected from the surface of the sample 100 and uses that information to determine the parts per million of an element within that sample. Basically, the OES machine obtains a total signal intensity for the element to be tested for, for example copper, and then divides that signal intensity by the total signal intensity for iron to obtain a ratio. This ratio is then used by the OES machine, via a lookup table or the like, to determine the PPM of copper within the sample.

However, as described above, because of the issues surrounding cadmium, to date no manufacturer of OES machines is capable of calibrating the OES machines to properly determine PPM of cadmium in a sample. An embodiment of the present invention allows this calibration to be completed so that OES can be used reliably to quickly determine the PPM of cadmium in a sample.

Because the spectroscopic wavelengths of elements, such as cadmium are known (See Table 1 setting forth examples of elements and their spectroscopic wavelengths), an OES machine is capable of detecting the signal intensity with respect to each of those elements.

TABLE 1

| ELEMENT | WAVELENGTH (nm) | ORDER | TYPE | INTERFERENCES |
| --- | --- | --- | --- | --- |
| Cadmium | 214.438 | 1 | ion | Pt, Ir |
| Copper | 324.754 | 1 | atom | Nb, U, Th, Mo, Hf |
| Lead | 168.215 | 1 | ion | Co |
| Iron | 238.204 | 1 | ion | Ru, Co |

Of course, other wavelengths are known and may be employed by various OES machines for each of the elements listed in Table 1. The selection of the appropriate wavelengths to be used by the respective OES devices is a function of design choice by the manufacturer of the OES device. So long as the wavelength selection methodology is consistent for all elements to be detected the selected OES device will properly detect the signal intensity for each respective element present in the sample 100.

Figure 2:
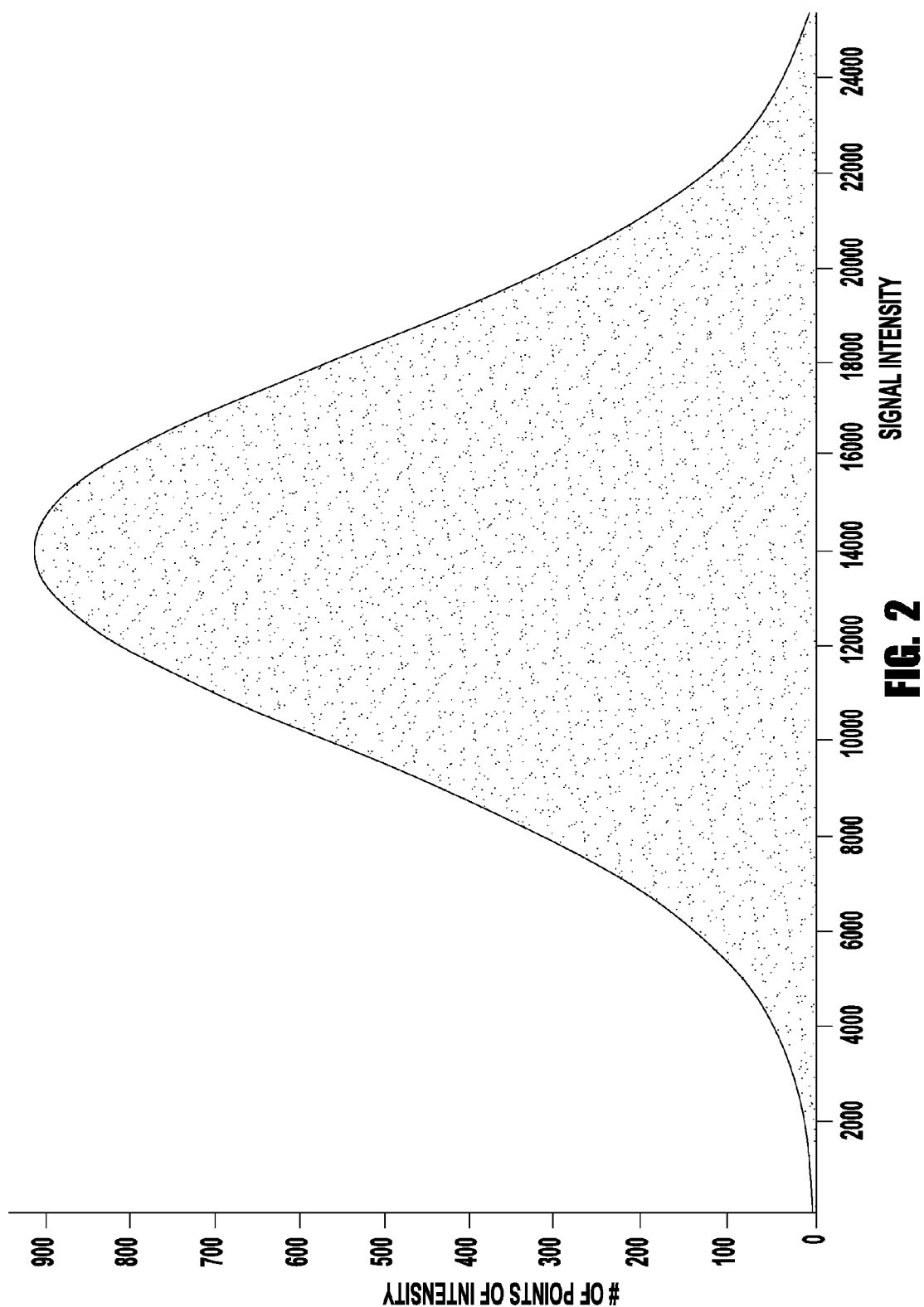
FIG. 2 illustrates a diagrammatical representation of the signal intensity of cadmium detected in a sample in accordance with an embodiment of the invention.

FIG. 2 depicts a signal intensity analysis of cadmium in an exemplary sample 100. As can be seen, the signal intensity of the sample is about 14,000 (which is a unit less measurement). This signal intensity is then divided by the signal intensity of iron for the same sample (not shown). This ratio of cadmium signal intensity/iron signal intensity is then recorded. The same sample 100 is then tested via another means, such as ICP-MS testing to determine the actual PPM of cadmium in the sample and the PPM of iron in the sample. The recorded ratio from the OES system can then be associated with the measured PPM of cadmium from the ICP-MS system. This essentially creates a correspondence chart/relationship between signal intensity from the OES type system to PPM measured using a different methodology, such as ICP-MS.

This process is then repeated for samples with varying levels of cadmium so as to obtain a plurality of data points. First, samples 100 are produced and tested to obtain the signal intensity ratios described above and then the samples are tested in a system such as ICP-MS to determine the PPM of the cadmium. These relationships/correlations are recorded.

Once a sufficient number of data points are recorded, a best fit curve can be generated to represent the relationship between cadmium signal intensity and cadmium PPM so that the OES device can be sufficiently calibrated and/or programmed to immediately determine the PPM of cadmium within a sample.

In an embodiment of the present invention, the best fit curve is presumed to be linear because the levels of cadmium to be detected are at or below 100 PPM. At such low levels, assuming that the curve is linear can provide desired reliability regarding cadmium PPM readings in a test sample. The number of data points collected and used to obtain the best fit curve are a function of the desired accuracy of the OES system employed. In an embodiment of the invention, at least ten (10) data points are used, in each of which the amount of cadmium varies.

In an embodiment of the invention, during the calibration process enough cadmium is placed into the sample 100 to compensate for light scattering effects during the OES process. As is known by those of ordinary skill in the art, reflected light from a sample can be scattered across various wavelengths. (That is, although theoretically an element has a single spectroscopic wavelength—see Table 1—the element may reflect light within a wavelength range). Because of this, it is possible to detect at least some signal intensity which appears to indicate the presence of cadmium in a sample which may have no cadmium. For example, a sample 100 having no cadmium may show a cadmium signal intensity of about 250. This can occur because of light scattering from other detected elements, which are not cadmium. Accordingly, a level of cadmium should be chosen in each sample 100 so as to exceed this light scattering effect (or "noise"). This amount is within the level of those skilled in the art.

By calibrating an OES system or device in accordance with the above methodology, an OES system can be used to quickly and accurately determine the levels of cadmium, in PPM, in a sample. This methodology is considerably quicker and less toxic than using ICP-MS methods, thus creating a more efficient certification process.

Figure 3:
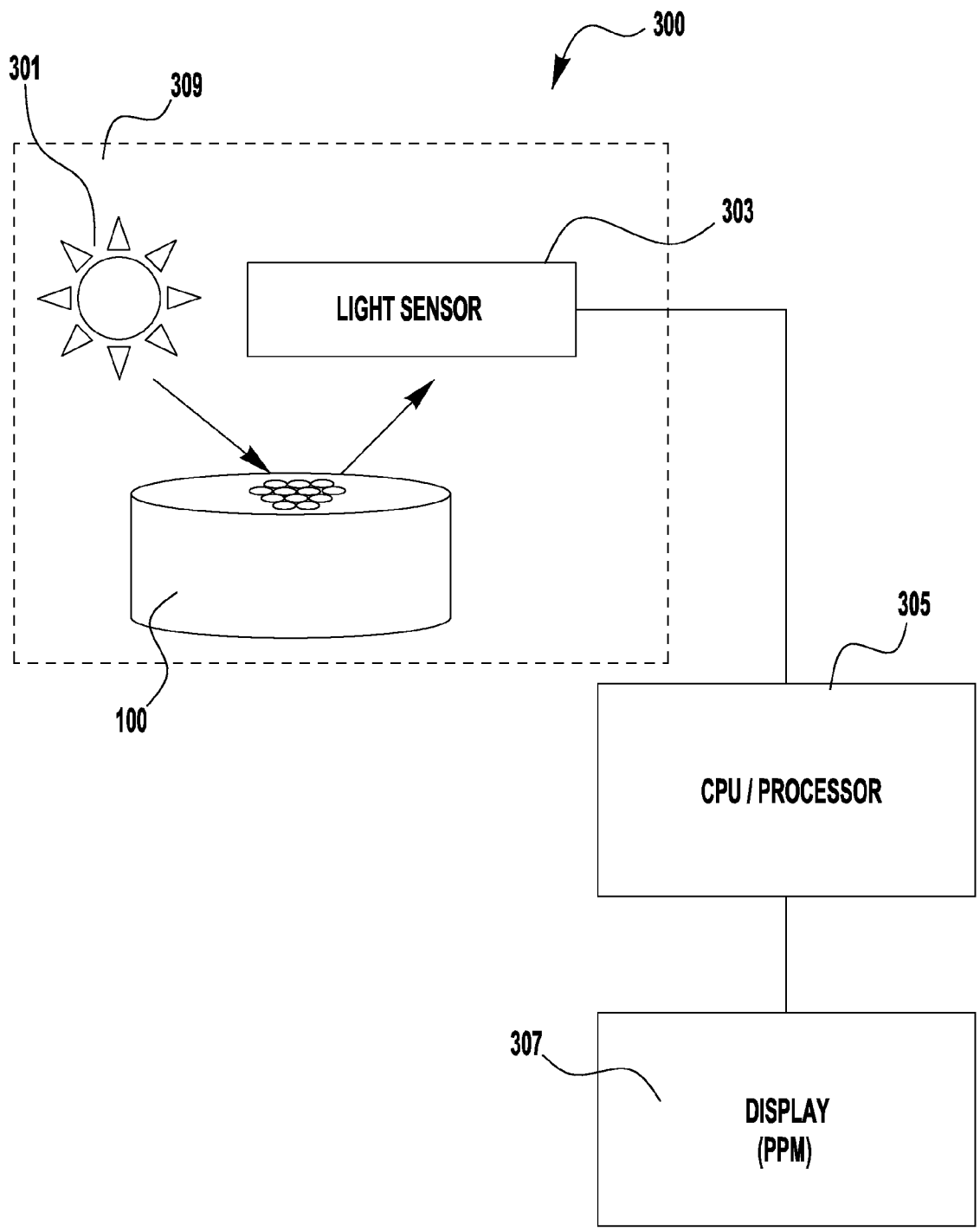
FIG. 3 illustrates a diagrammatical representation of an optical emission spectroscopy system in accordance with an embodiment of the present invention.

FIG. 3 is a simplified diagrammatical representation of an OES system 300 in accordance with an embodiment of the present invention. The configurations, structures and operations of OES systems capable of being employed with the present invention are known and understood by those of ordinary skill in the art, and a detailed discussion of their structure and operation will not be set forth herein. FIG. 3 is merely intended to provide a visual representation for the following discussion.

As shown, the sample 100 is placed within a testing portion 309 of the system 300. The sample 100 is sized, prepared and treated as required by the OES system 300 being employed. Within (or adjacent to) the testing portion 309 of the system 300 is a light source 301 which generates high light intensity plasma. In fact, as is known, thousands of individual arcs or plasma generations are made. The light from the plasma arcs is directed towards the surface of the sample 100. After the light impinges on the surface of the sample 100 it is reflected towards at least one light sensor 303. The reflected light will be made up of a plurality of wavelengths, where each wavelength represents a specific element within the sample 100. The illumination and collection can take about 30 seconds. The information regarding the reflected light is passed to a cpu/processor 305 which determines the relative light intensity for each element to be detected. Based on the level of light intensity detected for each element, such as cadmium, as compared to the level of light intensity for iron (being used as the reference) the cpu/processor 305 determines a PPM for the element detected. This information is then displayed on display 307 and can be printed out, etc. Although the above discussion employs iron as a reference, other base elements can be used. For example, copper, nickel, or tin can be used as a reference. Because all of the reflected wavelengths are collected at the same time, it is practical to determine the ratio of the of the reference element to the elements to be detected for (such as cadmium, etc.). By employing the ratio methodology, the OES system can normalize the data and reduce error. In another exemplary embodiment, it is also possible for the materials to be run on absolute intensity of the element to be run. In such an embodiment, the direct measurement of the element, such as cadmium, is possible with a shorter overall analysis time and with only a slight increase in the analysis error. Calibration by direct or absolute intensity enables the use of the OES system as a screening tool irrespective of the amount of a ratioing element present. That is, this embodiment of the present invention allows for the calibration and detection of an element, such as cadmium, within a different base material, such as nickel, than the base material used for the initial calibration, such as iron. For example, if an iron based sample was used to calibrate the OES system (as discussed above), the use of a direct or absolute intensity analysis will allow for the screening of elements, such as cadmium, in a sample having a different base element, such as nickel instead of iron, without having to conduct an entire calibration exercise with nickel based samples. Of course, although the evaluation process is quicker, because calibration is avoided, the detection can become less accurate and may be more appropriately utilized in screening operations.

During the calibration process, as described previously, the data points from the testing of samples containing varying levels of cadmium are input into the cpu/processor 305 in accordance with the software/programming of the system 300. Accordingly, upon completion of the calibration process the system 300 is capable of accurately and quickly determining the amount of cadmium in PPM of any test sample for certification. This can be done by employing a look-up table, a generated algorithm, a generated best-fit curve, or any other commonly know or used methodology. The present invention is not limited in this regard.

It is noted that the present invention not limited to the type or manufacture of the OES system employed, but can be used with any known or used OES system which is capable of detecting elements in metallic samples. Further, the present invention is not to be limited to applications involving cadmium, as the overall methodology described herein may be used for the detection of any elements having similar issues to that described herein.

While the invention has been particularly shown and described with reference to exemplary embodiments thereof, the invention is not limited to these embodiments. It will be understood by those of ordinary skill in the art that various changes in form and details may be made therein without departing from the spirit and scope of the invention as defined by the following claims.

What is claimed:

1. A method of detecting cadmium using an optical emission spectrometer, said method comprising:
   preparing at least one calibration sample which comprises a first element, at least one of lead, thallium and zinc, and a preselected amount of cadmium;
   calibrating said optical emission spectrometer to detect an amount of cadmium using said at least one calibration sample; and
   using said calibrated optical emission spectrometer to detect an amount of cadmium within a sample,
   wherein said at least one calibration sample further comprises copper coating layer that separates said first element from said at least one of lead, thallium and zinc, and a preselected amount of cadmium.

2. The method of claim 1, wherein said first element is iron.

3. The method of claim 1, wherein a plurality of said calibration samples are used during said calibration step, and wherein each of said plurality of samples contains a different preselected amount of cadmium.

4. The method of claim 1, wherein said at least one calibration sample comprises at least 40 percent by mass of said first element.

5. The method of claim 1, wherein said at least one calibration sample contains at least one welding electrode.

6. The method of claim 1, wherein said at least one calibration sample further comprises at least one of an iron and steel ingot.

7. A method of calibrating an optical emission spectrometer, said method comprising:
   preparing at least one calibration sample which comprises a first element, at least one of lead, thallium and zinc, and a preselected amount of cadmium; and
   calibrating said optical emission spectrometer to detect an amount of cadmium using said at least one calibration sample,
   wherein said at least one calibration sample further comprises copper coating layer that separates said first element from said at least one of lead, thallium and zinc, and a preselected amount of cadmium.

8. The method of claim 7, wherein said first element is iron.

9. The method of claim 7, wherein a plurality of said calibration samples are used during said calibration step, and wherein each of said plurality of samples contains a different preselected amount of cadmium.

10. The method of claim 7, wherein said at least one calibration sample comprises at least 40 percent by mass of said first element.

11. The method of claim 7, wherein said at least one calibration sample contains at least one welding electrode.

12. The method of claim 7, wherein said at least one calibration sample further comprises at least one of an iron and steel ingot.

13. The method of claim 7, further comprising using ratio of a detected signal intensity of cadmium to a detected signal intensity of said first element for said calibration step.

14. A method of detecting cadmium in a weld sample, said method comprising:
   calibrating an optical emission spectrometer to detect an amount of cadmium using at least one calibration sample which comprises a first element, at least one of lead, thallium and zinc, and a preselected amount of cadmium;
   placing a weld sample in said optical emission spectrograph;
   detecting a signal intensity for cadmium in said weld sample;
   detecting a signal intensity for a first element in said weld sample corresponding to said first element in said at least one calibration sample;
   determining at least one of a ratio of the signal intensity for cadmium to the signal intensity for the first element in said weld sample and a direct signal intensity for said cadmium in said weld sample; and
   determining an amount of cadmium in said weld sample using said at least one of said ratio and said direct signal intensity,
   wherein said at least one calibration sample comprises a copper coating layer that separates said first element in said at least one calibration sample from said at least one of lead, thallium and zinc, and a preselected amount of cadmium in said at least one calibration sample.

15. The method of claim 14, wherein said first element in said at least one calibration sample is iron and said first element in said weld sample is iron.

16. A calibration sample, said sample comprising:
   a matrix portion which comprises lead and a preselected amount of cadmium; and
   at least one ingot portion which contains iron;
   wherein said matrix portion is separated from said at least one ingot portion by a coating layer, and
   wherein said coating layer is copper.

17. The calibration sample of claim 16, wherein said calibration sample contains at least 40% by mass of iron.

18. The calibration sample of claim 16, wherein said calibration sample contains a plurality of ingot portions.

* * * * *